United States Patent [19]

Merril

[11] Patent Number: 4,555,490

[45] Date of Patent: Nov. 26, 1985

[54] RAPID VISUALIZATION SYSTEM FOR GEL ELECTROPHORESIS

[75] Inventor: Carl R. Merril, Rockville, Md.

[73] Assignee: The United States of America as represented by the Department of Health and Human Services, Washington, D.C.

[21] Appl. No.: 618,949

[22] Filed: Jun. 8, 1984

[51] Int. Cl.⁴ .................... G01N 21/77; G01N 33/52; G01N 33/68

[52] U.S. Cl. ........................................ 436/86; 436/94; 436/169; 436/174; 436/905

[58] Field of Search ....................... 436/86, 87, 88, 94, 436/164, 169, 515, 905, 174, 175, 176; 430/346, 616

[56] References Cited

U.S. PATENT DOCUMENTS 4,405,720  9/1983  Merril ............................ 436/169 X

FOREIGN PATENT DOCUMENTS 8203128  9/1982  World Intel. Prop. Org. ...... 436/86

OTHER PUBLICATIONS

Merril et al., Electrophoresis, vol. 3, pp. 17-23, 1982.
Merril et al., Anal. Biochem., vol. 110, pp. 201-207, 1981.
Merril et al., Proc. Natl. Acad. Sci. USA, vol. 76, No. 9, pp. 4335-4339, Sep. 1979.
Switzer et al., Anal. Biochem., vol. 98, pp. 231-237, 1979.
Merril et al., Science, vol. 211, pp. 1437-1438, Mar. 1981.
Langford, Basic Photography, Fourth Edition, pp. 161-163, 1977.
Mannheim, Photography Theory and Practice, Completely Revised and Enlarged Edition, pp. 303-330, 1970.

*Primary Examiner*—Barry S. Richman
*Assistant Examiner*—Robert J. Hill, Jr.
*Attorney, Agent, or Firm*—Holman & Stern

[57] ABSTRACT

A method using light ("photodevelopment") to develop a metallic silver image of biopolymers, particularly nucleic acids and proteins separated on polyacrylamide gels, whereby it is possible to visualize protein and nucleic acid patterns within 10 minutes after electrophoretic separation. This "photodevelopment" method requires only two solutions: a solution to "fix" the proteins and a solution containing silver ions, which produces an image when exposed to light. This type of protein stain has achieved a sensitivity of about 0.5 ng of protein. DNA separated on polyacrylamide may also be visualized with this stain.

10 Claims, 5 Drawing Figures

RAPID VISUALIZATION SYSTEM FOR GEL ELECTROPHORESIS

BACKGROUND OF THE INVENTION

1. Technical Field

The present invention is related to visualization of separated proteins and nucleic acids in suitable support medium. More particularly, the present invention is related to sensitive, simple and rapid visualization is biopolymer, preferably protein and nucleic acid, separated either on polyacrylamide gel or in thin membranes such as cellulose nitrate and the like.

2. Prior Art

One of the methods known for visualization of protein is described in U.S. Pat. No. 4,405,720. The stain described in this patent requires the use of three solutions and it takes a minimum of about 30 minutes to perform. Furthermore, the technique described in said patent does not stain proteins or nucleic acids in thin membranes such as cellulose nitrate.

Coomassie blue stain, the most commonly employed protein stain, takes hours to perform and it lacks the sensitivity to detect proteins present in low concentrations in biological fluids or tissues. Sensitivities achieved with heavy metal stains or fluorescent stains, on the other hand, were found to be less than, or at best, equivalent to Coomassie blue (about 10 ng of protein). Merril et al., Electrophoresis 1982, pp 327-342. Recently, more than a hundred-fold increase in sensitivity over that obtained with Coomassie staining was achieved by adapting a histological silver tissue stain for use with polyacrylamide gels. de Olmos, Brain, Behav. Evol. 2, 313-237 (1969), Switzer, et al Anal Biochem. 98, 231-237 (1979), Merril, et al Proc. Natl. Acad. Sci. USA 76 4335-4339 (1979). This stain could detect as little as a tenth of a nanogram of protein and an image could be achieved in less than 6 hours.

Histological silver stains were also adapted to visualize proteins separated by electrophoresis independently by two other groups; Kerenyi and Gallyas developed a stain for cerebrospinal fluid proteins separated on agarose Clin. Chim. Acta 38, 465-467 (1972), Clin. Chim. Acta 47 425-436 (1973) and Hubbell et al used a silver stain which was specific for nucleolar proteins Cell Biology Int'l Rep. 3, 615-622 (1979), Lischwe, et al Life Sciences 25 701-708 (1979).

The Kerenyi and Gallyas stain did not achieve widespread acceptance for a number of reasons. It was a histological stain adapted for use in agarose; it did not work well in polyacrylamide and it produced numerous staining artifacts. Merril, et al Anal. Biochem 110, 201-207 (1981), Verheecke, J. Neurol. 209, 59-63 (1975). In addition, there was a report of its quantitative irreproducibility. Verheecke, J. Neurol. 209, 59-63 (1975). Recent work by Peats has improved the Kerenyi stain performance in agarose resulting in a stain with linear protein concentration response from 0.2 ng/mm$^2$ to 2.5 ng/mm$^2$ and a reduction of artifacts. Peats, Biotechniques 1, 154-156 (1983).

In continuing the search for a means to simplify the methods for visualizing proteins, nucleic acids and other such entities separated on polyacrylamide gels, the Applicant reasoned that the selective reduction of silver from an ionic to a metallic form is the probable basis for both histological staining techniques and photography. Many early histological silver stains appear to have been derived from photographic methods. One of the pioneers of histological silver staining, Ranon y Cajal, credits his photographic experience with the revolutionary idea of using a photographic reducing agent (such as hydroquinone) to develop neuronal images in nervous tissue impregnated with silver nitrate. Gibson, Creative Minds in Medicine, 53-71 (1963). Recent histological silver stains have in general become more complex as empirical alterations have been made in the procedures to limit the staining to specific cells or subcellular structures. At the same time photographic image development has remained relatively simple, consisting of two steps: selective reduction of activated silver ions, followed by the removal of nonreduced silver ions. The selective reduction of silver ions may be performed by chemical reducing agents, chemical development, or by the use of light (photodevelopment).

Silver stains which have been used to visualize proteins separated on gels have utilized the "chemical development" of silver for visualization of the protein patterns. By modifying photochemical procedures a series of simple "photochemical" stains were developed. U.S. Pat. No. 4,405,720; Merril, et al, (1981) supra; Merril, et al, Science 211, 1437-1438 (1981); Merril et al, Electrophoresis 3, 17-23 (1982). These stains employed formaldehyde as the silver ion reducing agent in an alkaline solution containing sodium carbonate. The formaldehyde is oxidized to formic acid while reducing the ionic silver to metallic silver. Merril et al, (1981) supra. The formic acid produced in this process is neutralized by the sodium carbonate in the developing solution, thereby maintaining the alkaline conditions.

Silver stains utilizing photographic "chemical development" techniques have been shown to be over 100 fold more sensitive than Coomassie blue staining; they use minimal amounts of expensive reagents, and polypeptide images may be obtained within 50 minutes. Merril, et al, Anal. Biochem. 110, 201-207(1981), Science 211, 1437-1438(1981), Electrophoresis 3, 17-23(1982). Many variations of silver staining methods employing "chemical development methods" have been recently derived. These have been reviewed by Dunn and Burghes, Electrophoresis 4, 173-189(1983). It should be noted, however, that a sensitive, simple and rapid system for visualization of separated proteins and nucleic acids, both in gel electrophoresis and in thin membranes, has simply not heretofore been known in the art to which it pertains.

SUMMARY OF THE INVENTION

It is, therefore, an object of the present invention to provide a sensitive, simple and rapidly developing visualization system for any substance or biopolymer that affects the rate of oxidation or reduction of silver relative to the support medium based on the photodevelopment of ionic silver to form a visible image in a suitable separation medium or on a suitable matrix.

It is a further object of the present invention to provide a single solution photoimaging mixture for immediate visual detection of biopolymers when the biopolymer is present at a suitable concentration in the separating matrix.

Other objects and advantages will become apparent as the description of the present invention proceeds.

BRIEF DESCRIPTION OF THE DRAWINGS

These and other objects, features and many of the attendant advantages of the invention will be better understood upon a reading of the following detailed description when considered in connection with the accompanying drawings wherein.

Dilutions of this initial solution used were 100×; 200×; 400×; 800×; 1,600×; 3,200×; 6,400×; 12,800×; 25,600×.

Figure 2A:
Figure 2B:

FIG. 2 shows comparison of equivalent two-dimensional gels containing E. coli proteins. Each gel contained 20 μg total protein. Gel "A" was stained by silver using chemical development, 116 proteins were observed in the region illustrated. Gel "B" was stained by silver using photodevelopment stain. 83 proteins were observed in the region illustrated.

Figure 3A:
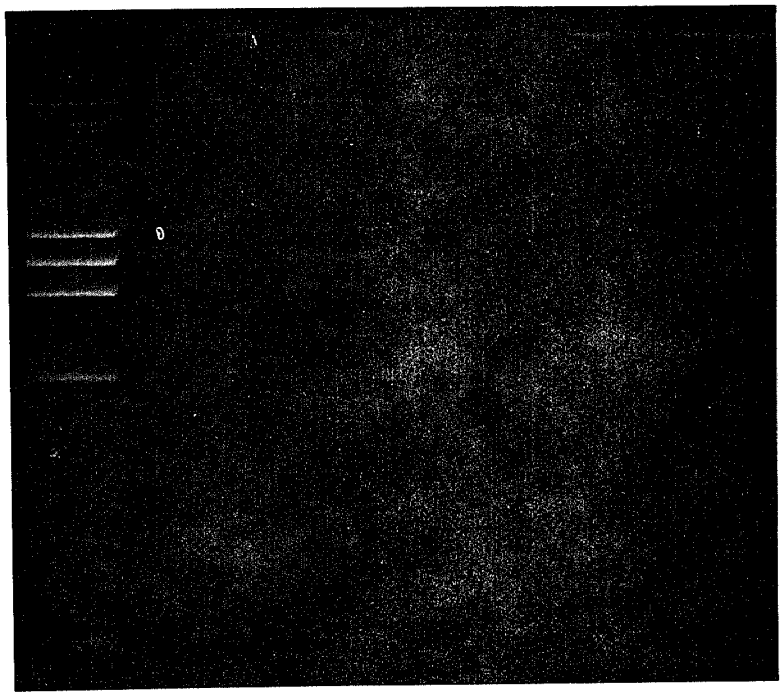
Figure 3B:
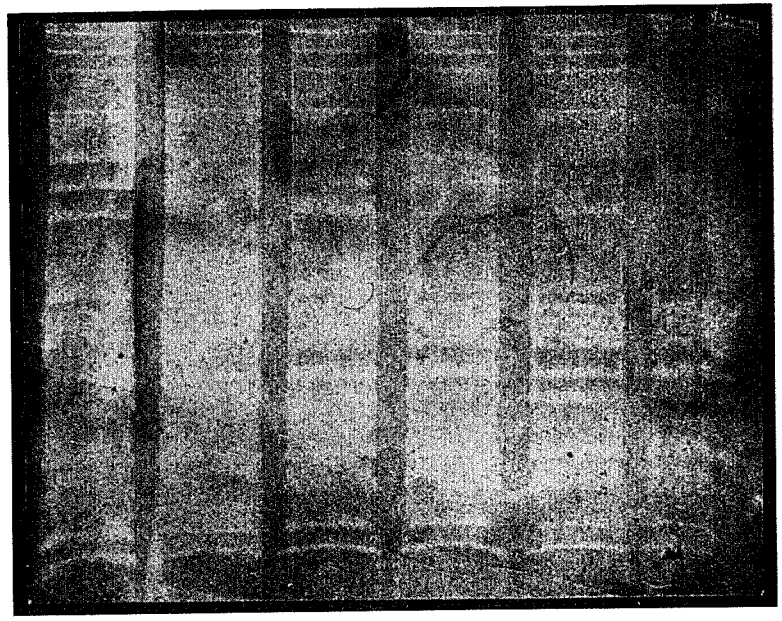

FIG. 3 shows photodevelopment silver stain of a polyacrylamide gel containing DNA fragments. The DNA is φX174, Hae III fragments (25.1% of 904 K, MW: fragments 20% of 721 K, MW fragments; 16.2% of 583 K, MW fragment; 11.2% of 403 K, MW fragments; 5.8% of 207 K, MW fragment; 5.2% of 188 K, MW fragments; 5% of 181 K MW fragments; 4.4% of 156 K, MW fragment; 3.6% of 130 K, MW fragment; 2.2% of 79 K, MW fragments; and 2.2% of 48 K, MW fragments. The wells contained 500 ng, 250 ng, 150 ng, 125 ng, 75 ng and 37.5 ng of total DNA, respectively.

Figure 4:
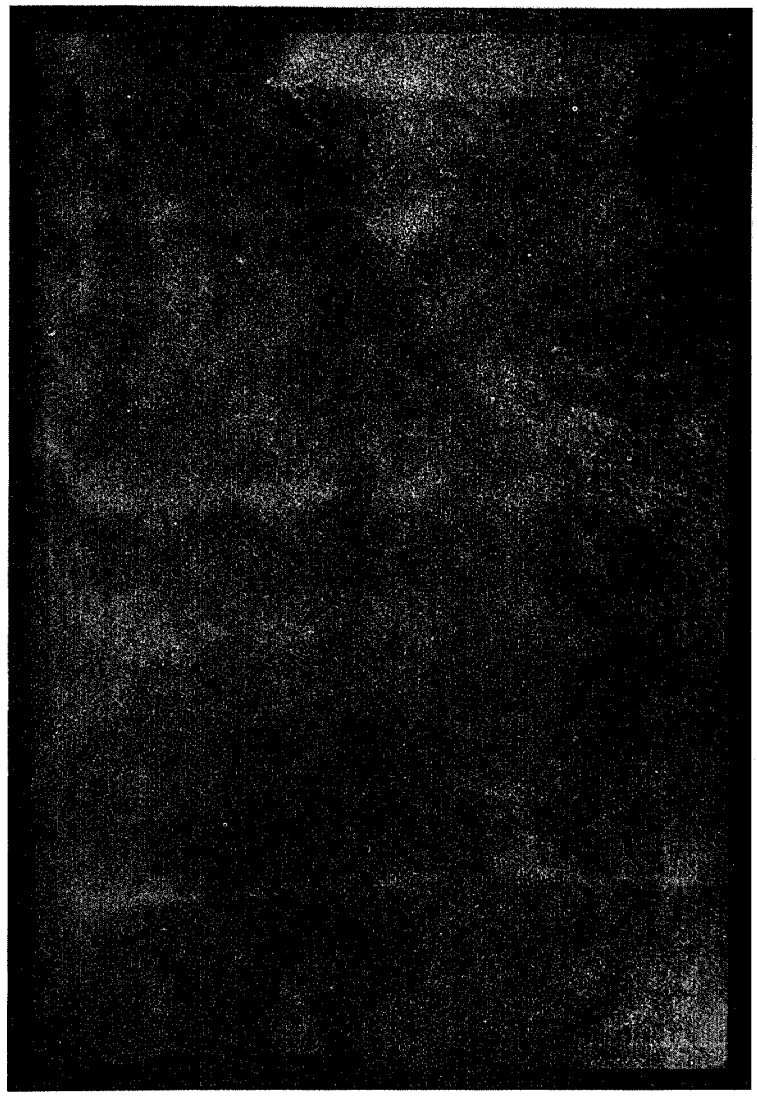

FIG. 4 shows photodevelopment silver stain of proteins blotted onto a cellulose nitrate membrane. The most concentrated well (1) contained 16 μg of phosphorylase b, 21 μg of BSA, 37 μg of ovalbumin, 21 μg of carbonic anydrase, 20 μg of trypsin inhibitor and 30 μg of a lactalbumin. Wells 2, 3, 4, and 5 each contained 50% less protein than the previous one. The relative concentrations of each protein in well 5 were 1, 1.3, 2.3, 1.3, 1,3, and 1.9 μg, respectively.

Figure 5A:
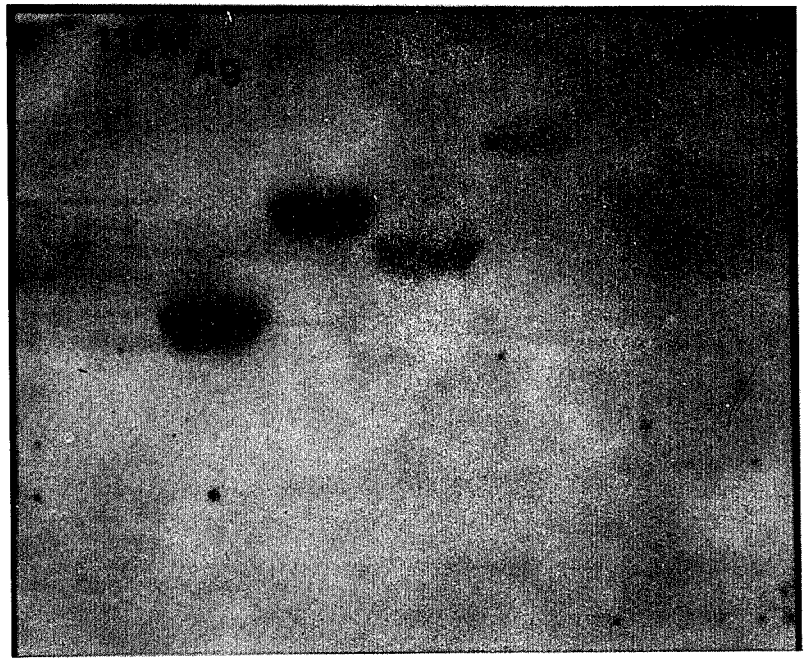
Figure 5B:
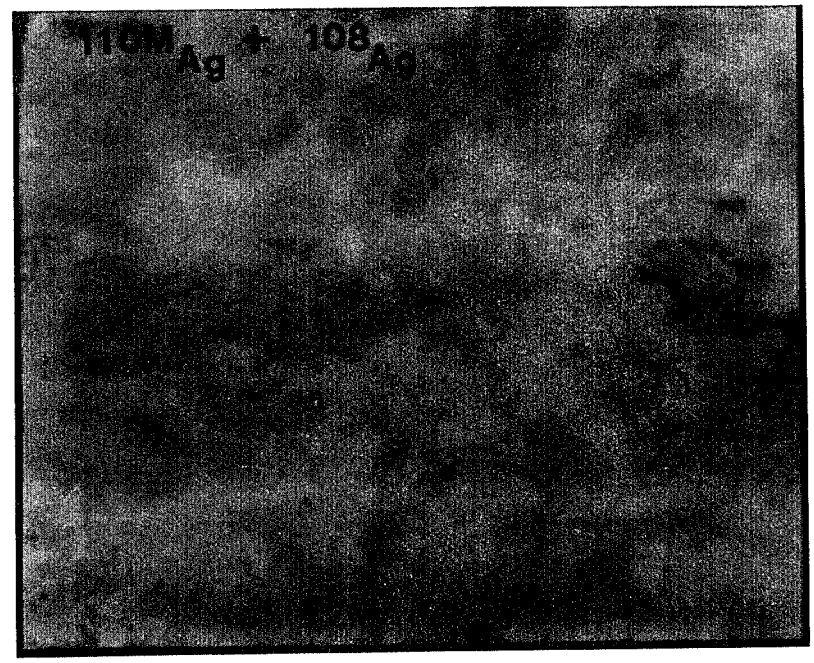

FIG. 5 shows autoradiography of an electrophoretic gel in radioactive silver nitrate (radioactive silver, $^{110M}Ag$). The upper image (a) was prepared by placing a gel containing five purified proteins separated in one dimension in a solution containing $10^{-9}M$ $AgNO_3$ (with $^{110M}Ag$). Autoradiography was performed by placing the wet gel in a plastic bag and then placing individually wrapped X-ray film over this preparation for a timed exposure. The lower image (b) was made by equilibrating the same gel as that visualized in the upper image (a) in a solution containing 0.1M silver nitrate. (Nonradioactive silver nitrate was added to the $10^{-9}M$ $AgNO_3$ solution to bring the final concentration of silver nitrate to 0.1M overnight). Autoradiography was again performed, as described herein.

DETAILED DESCRIPTION OF THE INVENTION

The above objects and advantages in accordance with the present invention are achieved by a process for rapid visualization of separated biopolymers on suitable support medium comprising:

(a) fixing said support medium for about 5 min with about 50% v/v methanol, about 10% v/v acetic acid and about 40% v/v of deionized water containing about 2% w/v citric acid and about 0.2% w/v sodium chloride;

(b) rinsing said support medium rapidly with deionized water;

(c) placing said support medium in a solution containing about 50% v/v methanol, about 10% v/v acetic acid and 40% v/v of deionized water containing about 2% w/v silver nitrate; and (d) illuminating said support medium with uniform light, wherein imaging of separated biopolymers appears in less than about 10 minutes.

The term "visualization system" as employed herein includes all those ingredients and components which are essential for photoimaging of the electrophoretically separated entities, e.g. proteins, nucleic acids and the like. The term "support medium" as used herein refers to any medium suitable for loading the entities which need to be separated by electrophoresis or other separating techniques. Examples of such supporting medium include agarose, polyacrylamide gels, discs, plates, thin membranes and the like. Examples of thin membranes include cellulose nitrate, cellulose acetate, nylon, glass or glass fibre and similar matrices.

Illumination include exposure of the support medium loaded with isolated entities to uniform visible or ultraviolet or any other suitable light. Such illumination may be continuous, intermittant or a combination of light-dark cycle including exposure to room light. Illumination with shorter wavelength (higher energy) radiation, e.g. ultra violet (UV) is more efficient in producing the image. However, short wavelength UV often causes the background to appear rapidly and darken, thereby soon obscuring the biopolymers.

Any material or method suitable for gel or thin membrane electrophoresis may be utilized for the practice of this invention. However, the preferred materials and methods are described hereunder.

Materials and Methods

1. Chemicals

Acrylamide, N,N'-methylenebisacrylamide, sodium dodecyl sulfate (SDS), N,N,N',N'-tetramethylethylenediamine (TEMED), ammonium persulfate, Biolyte carrier ampholytes, agarose and Coomassie Brilliant Blue R-250 were purchased from Bio-Rad Corporation. 2-Mercaptoethanol was obtained from Eastman Kodak Co. Tris base, glycine and citric acid were from Sigma Chem. Co. Silver nitrate, glycerol, sodium chloride, acetic acid, methanol and anhydrous sodium carbonate were obtained from J. T. Baker & Co. Silver nitrate containing radioactive silver ($^{110M}Ag$, 116Ci/M) was obtained from Amersham Radiochemicals Inc. Purified molecular weight marker protein kits were obtained from Pharmacia Pharmaceuticals. φX174 DNA HAE III fragments were from Bethesda Research Laboratory.

2. Standard proteins and cellular proteins

Protein standards (Pharmacia) used in the dilutional studies were: phosphorylase b, bovine serum albumin, ovalbumin, carbonic anhydrase, soybean trypsin inhibitor, and α-lactalbumin. E. coli proteins were obtained from bacteria grown in M56 minimal media supplemented with amino acids and glucose. E. coli were grown to a density of $2 \times 10^8$ cells/ml and then centrifuged 2 min at $12,500 \times g$. The supernatant was discarded and the pellet resuspended in an equal volume of protein solubilization solution (see infra) and heated to 95° C. for 4 min. The mixture was chilled on ice and again centrifuged at 12,500×g for 2 min. The supernatant was stored at −70° C. *E. coli* lysate protein concentrations were determined by the method of Lowry et al., *J. Biol. Chem.* 193, 265–275 (1951) which is incorporated herein by reference.

3. Protein polyacrylamide gel electrophoresis and protein blotting

Polyacrylamide electrophoresis was performed in the presence of 1% SDS in a 10% polyacrylamide gel. The discontinuous buffer system described by Laemmli, *Nature*, 227, 680–685 (1970) which is incorporated herein by reference was used to separate proteins by molecular weight. Proteins were placed in wells cast into the stacking gel. Bromophenol blue dye was used for tracking and the current was turned off when the dye front reached 2 mm from the bottom of the gel.

Gels were then either stained or transblotted onto nitrocellulose membranes. Western blotting was performed in a transblotting cell (Bio-rad) containing a 25 mM Tris-HCl, 192 mM blycine buffer pH 8.3 with 20% v/v methanol. Transblotting was performed for 10 hours with a constant current of 250 mA at 70 volts. The nitrocellulose membrane contained 0.45 mu pores (Millipore, type HAWP 00010, Lot C7K 12560A).

4. Two-dimensional electrophoresis

Two-dimensional electrophoresis was performed according to O'Farrel, *J. Biol. Chem.* 250, 4007–4021 (1975) which is incorporated herein by reference, using isoelectric focusing (4:1 mixture of carrier ampholytes of pH range 5–7 and 3–10) in the first dimension and electrophoresis through a uniform gel of 10% acrylamide in the second dimension. Protein samples were solubilized in a solution containing 2% w/v SDS, 5% v/v mercaptoethanol, 20% v/v glycerol, 2% v/v carrier ampholytes, pH 3–10, and 2% v/v Triton X-100.

5. DNA polyacrylamide gel electrophoresis

Polyacrylamide gel electrophoresis was performed in the presence of 0.2% SDS in 0.8 mm thick slab gels of 5% acrylamide. The ratio of acrylamide to N,N'-methylene bis acrylamide was 29:1. Gels and running buffer were prepared with 0.34M tris, 0.44M boric acid and 16 mM EDTA. Gels were polymerized with ammonium persulfate and TEMED and were prepared with 1 cm wide wells. The DNA applied was $\phi$X174, HAE III restriction digest fragments. Electrophoresis was carried out at 10 mA/gel until a bromophenol blue dye front reached the bottom of the gel.

6. Quantitative analysis and image enhancement

Quantitation was performed by photographing stained gels next to a calibrated photographic density standard (from the National Bureau of Standards) with 35 mm Tri-X film (Eastman Kodak). A uniform light source, a 160-W fluorescent grid lamp with a clear lucite diffusion screen (Model T-12, Aristo Grid Lamp Products, Inc.) was used for illumination. Photographic images were scanned at a resolution of 100 $\mu$m with an Optronics 1000HS scanning densitometer at the 0–2 optical density setting. Image densities were normalized for variations in photography and densitometric digitization with the calibrated photographic density standards. Density in this analysis is defined as it is in photographic usage; that is: one unit of density is a density that permits the transmission of one percent of the incident light. The density scale used is logarithmic so that a density of 2 permits transmission of only a tenth of a percent of the light. About 6.5 ng of silver per mm$^2$ of photographic gel emulsion corresponds to a density of one unit. Wall, et al., *Photographic Facts and Formulas*, p. 85, (1976). Analysis was performed with an image processor (DeAnza Systems, Inc., model IP5000) and a PDP 11/60 computer (Digital Equipment) as described in Goldman et al, *Clin. Chem.* 28, 1021–1025 (1982) which is incorporated herein by reference. Proteins visualized on the gels by silver staining were quantitatively analyzed by outlining each digitized protein image with a polygon, adjusted so that it closely surrounded each protein band. The densities of all of the picture elements within the polygon were measured and the average density computed and multiplied by the total area bounded by the polygon.

In studies to determine the minimal amount of protein that can be visualized by a specific stain, the digitized images were enhanced by expanding the range of luminous intensity within a subject of the total gray scale for each area of a gel that was of specific interest.

7. Chemical development silver stain

Polyacrylamide electrophoresis gels (PAGE) were fixed for 20 minutes in a solution of 50% v/v methanol and 10% v/v acetic acid, followed by rehydration for 20 minutes in a solution containing 10% ethanol and 5% acetic acid (v/v). Gels were then soaked for 5 min in a solution containing 0.0034M potassium dichromate and 0.0032N nitric acid, followed by immersion in 0.012M silver nitrate for 20 min. The gels were then rinsed with agitation in a solution containing 0.28M sodium carbonate and 0.5 ml of formaldehyde (37% commercial formaldehyde) per liter. This last step required at least two changes of the solution to prevent precipitated silver salts from adsorbing to the surface of the gel. Development was usually stopped when a slightly yellowish background appeared with a solution of 3% v/v acetic acid for 5 min. Gels were then washed twice for 10 min with water. They were then stored in water or soaked in 3% glycerol for 10 min and then dried between dialysis membrane (Bio-Rad) under a vacuum at 80°–82° C. for 3 h. This latter procedure results in a transparency which is relatively permanent. Reagent concentrations and procedure times given above have been optimized for 0.8 mm thick PAGE gels. Thicker gels require adjustments of reagent concentrations and timing.

8. Photodevelopment silver strain

Electrophoretic gels were fixed for 5 minutes with about 200 ml of a 50% v/v methanol, 10% v/v acetic acid, 40% v/v of deionized water solution, containing 2% w/v citric acid and 0.2% w/v sodium chloride. The gels were then rinsed briefly with about 200 ml of deionized water to remove surface chloride and placed in about 200 ml of a solution containing 50% methanol v/v, 10% v/v acetic acid and 40% v/v of deionized water containing 2% w/v silver nitrate. The gels immersed in this solution were then illuminated by placing them about 2.5 cm from a uniform light source, e.g. fluorescent grid lamp described, supra, until the image appeared. Serial photographs were taken during image development. Image development may be stopped at any point by removing the gel from the light source and storing the gel in the dark. Nitrocellulose protein blots were stained with the photodevelopment silver stain in a manner similar to that employed for the PAGE gels, however, considerable improvement was noted in the protein image if the nitrocellulose blots were exposed to transillumination with the fluorescent grid lamp for 10 minutes followed by 1 hour in normal room lighting.

Image preservation of photodevelopment stained gels is difficult. Storage of silver stained gels in the dark is sufficient only for temporary preservation. Long term preservation may be achieved by three rinses in a solution containing 5% v/v acetic acid and 50% v/v methanol (10 minutes per rinse) followed by storage in a fresh solution of similar composition. Archival storage of the image is better achieved by photographing the gel.

Results

1. Sensitivity

Figure 1A:
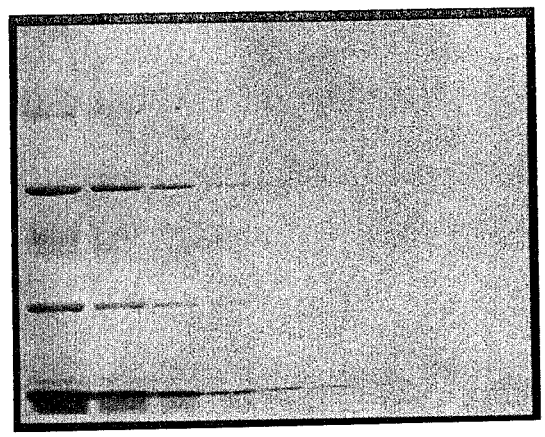
FIG. 1 shows stoichiometric response of: A-Coomassie blue, B-photodevelopment silver stain, C-Chemical development silver stain. The proteins (Pharmacia Purified Molecular weight markers) were separated by SDS gel electrophoresis. Proteins in the initial solution were: Phosphorylase b: 320 μg/ml, Bovine serum albumin 415 μg/ml, ovalbumin 735 μg/ml, carbonic anhydrase 415 μg/ml, trypsin inhibitor 400 μg/ml and lactalbumin 605 μg/ml.
Figure 1B:
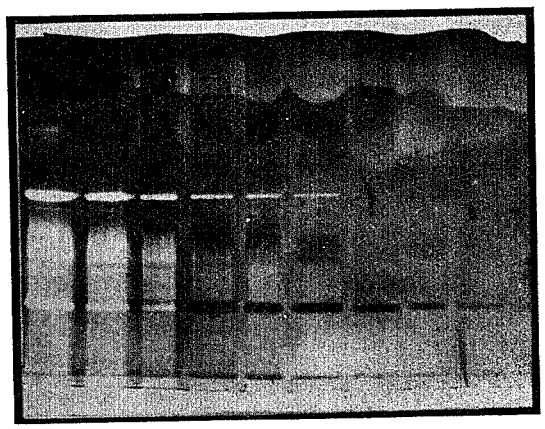
Figure 1C:
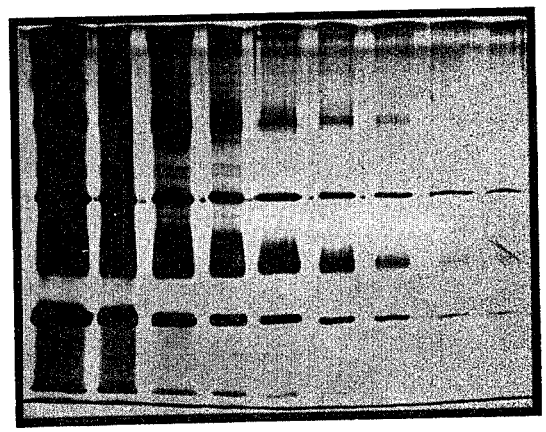

Table 1 and FIG. 1 compare the sensitivity achieved with the photodevelopment silver stain of the present invention, Coomassie Brilliant Blue R-250, and a "chemical development" silver stain.

TABLE 1

Sensitivity comparison of photodevelopment, chemical development and Coomassie blue

| Protein[a] | Sensitivity limits in ng of protein[b,c] | | |
|---|---|---|---|
| | coomassie blue | photo-development | chemical development |
| Albumin | 5.0 | 1.03 | 0.5 |
| Ovalbumin | 18.0 | 1.80 | 0.09 |
| Carbonic anhydrase | >10.0 | 0.50 | 0.05 |
| Trypsin inhibitor | 5.0 | 0.50 | 0.05 |
| α-Lactalbumin | >15.0 | 1.50 | 0.75 |

[a]Proteins (Pharmacia purified molecular weight markers) were separated by SDS gel electrophoresis in a 10% polyacrylamide gel.
[b]Sensitivity was determined by serial diiutions of proteins on equivalent gels. Concentrations of proteins in the initial solution were: BSA: 103 μg/ml; OV: 184 μg/ml; CA: 104 μg/ml; ST: 100 μg/ml; LAC: 151 μg/ml. 10 μl of serially diluted solutions were electrophoresed. Dilutions used were: 100 x, 200 x, 1000 x, 2000 x, 10,000 x, 20,000 x, 100,000 x.
[c]Limits of protein detectable with these stains were either just visible to the eye, or visible by computer enhancement of the gel image as described supra. No protein band was detected with Commassie blue stain at the highest concentration of carbonic anhydrase or α-lactalbumin each of these proteins used in this set of serial dilutions (10 ng and 15 ng, respectively).

Purified proteins were serially diluted and electrophoresed on three equivalent polyacrylamide gels. The dilution range was chosen to span the region from the lower limits of protein concentrations reported for Coomassie Brilliant Blue R-250 (10 ng of protein) to the lower limits reported for silver stains (0.1 ng). Following electrophoresis the gels were stained with Coomassie Brilliant Blue R-250 or silver. The gels were photographed at timed intervals during silver staining and the gel images and their photographic images were scanned both by eye and by computer "contrast stretch" enhancement technique mentioned supra.

In general, the photodevelopment silver stain is more sensitive than Coomassie Brilliant Blue R-250, by a factor of 10 but less sensitive than the chemical development stain (FIG. 1). In a comparison of equivalent regions of two dimensional electrophoretic patterns of E. coli proteins, 83 protein spots could be visualized with the photodevelopment stain, while 116 spots were observed in the same region with the chemical development silver stain (FIG. 2). Coomassie blue revealed only 12 faintly stained spots (not illustrated) in this region. From comparative studies of specific regions of two dimensional gels, the photodevelopment stain is in general 72% as efficient as the chemical development stain for the visualization of proteins from complex cellular lysates.

2. Quantitative potential of silver stains

Comparisons were made between the stoichiometric response of the photodevelopment silver stain and a chemical development silver stain. The chemical silver stain displayed a linear relationship between optical density and protein concentration for the five proteins tested in this study, as demonstrated by the high correlation coefficients obtained by linear regression analysis (FIG. 2 and Table 2).

TABLE 2

A comparison of the quantitative potential of silver stains with five proteins.

| Protein[a] | Dilutional range of protein (ng) | Density range (OD × mm$^2$) | No. of points measured | Slope | Y intercept | Correlation coefficient |
|---|---|---|---|---|---|---|
| Chemical development | | | | | | |
| α-Lactalbumin | 1500–23 | 0.31–0.88 | 7 | 0.33 | 0.39 | 0.98 |
| Trypsin inhibitor | 4000–31 | 0.61–2.90 | 8 | 0.74 | 0.54 | 0.99 |
| Carbonic anhydrase | 260–16 | 0.56–2.77 | 5 | 0.57 | 8.78 | 0.99 |
| Ovalbumin | 1838–28 | 0.66–1.76 | 7 | 0.67 | 0.61 | 0.98 |
| Albumin | 519–16 | 0.99–3.42 | 6 | 0.95 | 4.97 | 0.98 |
| Photodevelopment | | | | | | |
| α-Lactalbumin | 1500–47 | 0.09–0.35 | 6 | 0.23 | 0.11 | 0.56 |
| Trypsin inhibitor | 1000–16 | 0.39–0.50 | 7 | 0.51 | −0.02 | −0.08 |
| Carbonic anhydrase | 4150–130 | 0.95–0.73 | 6 | 0.94 | −0.07 | −0.65 |
| Ovalbumin | 7350–230 | 0.43–0.39 | 6 | 0.44 | 0.00 | −0.48 |
| Albumin | 2075–65 | 0.85–2.17 | 6 | 0.84 | 0.62 | 0.98 |

[a]Proteins (Pharmacia purified molecular weight markers) were separated by SDS gel electrophoresis in a 10% polyacrylamide gel as illustrated in FIG. 2.
[b]Total OD was determined by multiplying the average optical density in each band by the measured area of the band in mm$^2$.

The stoichiometric response of the photodevelopment was analyzed over a range of protein concentrations in which the proteins demonstrated positively stained bands. However, the photodevelopment often produced negatively stained regions, even within positively stained bands. No attempt was made to correct for this negatively stained component that sometimes was present within a positive stained band. These negative components reduced the overall apparent protein density within the polygonal area occupied by the protein on the gel. While such negative staining effects are often observed with proteins which are stained to saturation, they also occurred in non-saturated regions with the photodevelopment. Some formulations of silver stain appear to consistently stain specific proteins in a negative manner as reported by Sammons, et al., *Electrophoresis* 2, 135-141 (1981). The quantitative difficulties in using stains which produce both negative and positive staining is illustrated by the poor correlation coefficients (obtained by a linear regression analysis of protein concentration variations and optical densities) with the photodevelopment stain.

3. Staining of DNA

DNA fragments separated in 5% polyacrylamide gels produce a negative image with the photodevelopment silver stain. This silver stain has approximately the same sensitivity as ethidium bromide. In contrast, the chemical development silver stains have proven to be more sensitive than ethidium bromide and give a positive image with DNA and RNA. Image development with the physical development silver stain progresses from an early phase with a whitish gray background to an image with a grayish-brown background. Contrasts obtained between the negatively stained DNA bands and the whitish-gray background are relatively poor during the first 10 minutes of image development. In general, bands containing DNA with the highest molecular weight DNA (207 K to 904 K) remained negatively stained, while the smaller fragments (188 K to 48 K) tended to become positively stained just prior to the obscuring effect of the background darkening. However, with very dilute DNA samples, the high molecular weight DNA also began to form a positive image, just prior to background darkening.

4. Staining of transblotted protein on nitrocellulose

Proteins transblotted onto nitrocellulose membranes were detectable as negative images (FIG. 4) within 10 minutes by staining with the photodevelopment silver stain of the present invention. However, although the bands could be seen by eye, the contrast between the bands and the background is marginal and not easily photographed. If the cellulose nitrate is taken off the light box and left for 1 hour in the silver nitrate solution, the contrast improves and as little as 0.5 ng of protein can be visualized.

It is apparent from the above, that previously described silver stains have relied primarily on the use of chemical reducing agents to reduce ionic silver to a metallic silver image. These stains are called chemical development silver stains. This is in contrast to the photodevelopment silver stain of the present invention in which ionic silver is believed to be reduced to metallic silver by the action of light energy. This photodevelopment silver stain is based on the observation that ionic silver is light sensitive. The observation that light could convert ionic silver to metallic silver was first published by Carl Wilhelm Scheele in 1777 when he demonstrated that silver chloride crystals exposed to light while under water produced hydrochloric acid and a black metallic silver precipitate. This ability of light to reduce ionic silver to metallic silver was adapted by William Fox Talbot, in 1839, as the basis of one of the first photographic processes. Talbot's process dominated photography from its introduction until 1862 when photodevelopment by light was replaced by "chemical development" processes.

As discussed above photographic "chemical development" processes have recently been successfully adapted as gel stains to form images of biopolymers separated by electrophoresis on gels. However, "chemical development" processes even in their simplest forms require at least two solutions (excluding the protein fixation step which precedes staining). The first solution, an acidic solution, contains silver nitrate. The second solution, an alkaline reducing solution, selectively reduces the ionic silver to produce a metallic silver image. Merril, et al., *Electrophoresis*, 3, 17-23 (1982). Most of the organic reducing agents only show a useful reducing activity in alkaline conditions. Attemps to use a single solution "chemical stain" in which the silver ions are present in the alkaline reducing solution usually results in the spontaneous reduction of silver ions.

The present invention has now made it possible to use a single solution with a photodevelopment stain. The stain as taught by the present invention permits the maintenance of silver ions in a relatively stable acidic solution eliminating the need for an alkaline reducing solution.

Single solution photodevelopment silver stain of the present invention has two major advantages over the two solution chemical development silver stains. First, pH gradient effects are eliminated. In a two solution stain, one solution (the acidic silver nitrate), diffuses out of the gel while the alkaline solution containing the reducing agent diffuses in. The interactions of these solutions create complex pH gradients within the gel. A single solution photodevelopment stain does not have such diffusion effects and this results in a reduction of staining artifacts due to variations in gel thickness or by the use of plastic gel "backings". Second, biopolymers bound to ultra-thin supporting membranes, such as cellulose nitrate, stain poorly with the "chemical stains" as they retain very little silver nitrate when they are transferred into the alkaline solution for image development. Since the photodevelopment stain contains the silver ions in the image developing solutions, it permits the visualization of biopolymers bound to thin membranes.

It should be understood, of course, that the employment of a "fixation" solution prior to silver staining protein or nucleic acid is essential for both the chemical and photodevelopment methods. Fixation solutions have a dual role in both methods: first, they "fix" or retard diffusion of the biopolymer from the gel or membrane, and second, they wash substances that might interfere with staining (such as reducing agents or detergents) from the gel or membrane. Electrophoretic systems which employ reducing agents and or detergents often require more than one "fixation" wash to clear the gel of these substances. The fixation solution in the photodevelopment method also has an additional role of impregnating the gel with chloride ions which are important for the process of the invention described herein.

A particularly advantageous aspect of the present invention is that the separated biopolymers can be visually detected almost instantaneously as soon as the separation matrix, e.g. polyacrylamide gel, is immersed in the photoimaging solution of the present invention. A fine bluish-white AgCl precipitate formed as a result of the interaction of silver with chloride ions permits immediate visualization of the biopolymer so long as the biopolymer is present in sufficient quantity, usually in micro or nanogram concentration. The whitish-blue precipitate is formed except in regions occupied by the biopolymer. These regions remain clear until illumination. Then they darken first.

It is further noted that the method of the present invention is applicable to staining and visualization of any substance including biopolymer that affects the rate of oxidation or reduction of silver relative to the support medium and is present either in isolated form or in thin tissue sections, smears and the like, e.g. in chromosomal banding. All that is necessary for vinitial visualization is the formation of silver chloride precipitate.

It is understood that the examples and embodiments described herein are for illustrative purposes only and that various modifications or changes in light thereof will be suggested to persons skilled in the art and are to be included within the spirit and purview of the application and the scope of the appended claims.

I claim:

1. In a method for separating biopolymer entities by thin membrane or polyacrylamide gel electrophoresis of the type including fixing the separated entities in a suitable fixing medium and thereafter rapidly rinsing the fixed gel with deionized water to remove the fixing medium, the improvement comprising having in said fixing medium about 2% w/v citric acid and about 0.2% w/v sodium chloride; and visualizing said separated entities in less than about 10 minutes by placing said gel or membrane in a single solution photoimaging mixture of 50% v/v methanol, 10% v/v acetic acid and 40% v/v deionized water containing 2% w/v silver nitrate and then uniformly illuminating said gel or membrane with visible light within any chemical treatment.

2. The method of claim 1, wherein said biopolymer entities are proteins or nucleic acids.

3. A process for rapid visualization of separated biopolymers on suitable support medium comprising:
   (a) fixing the biopolymers separated on said support medium for about 5 min in a fixing medium consisting esentially of about 50% v/v methanol, about 10% v/v acetic acid and about 40% v/v of deionized water containing about 2% w/v citric acid and about 0.2% w/v sodium chloride;
   (b) thereafter rinsing said support medium with deionized water to remove surface chloride;
   (c) placing said support medium in a single solution photoimaging mixture containing about 50% v/v methanol, about 10% v/v acetic acid and 40% v/v of deionized water containing about 2% w/v silver nitrate; and
   (d) illuminating said support medium with uniform light without any chemical treatment, wherein imaging of separated biopolymers appears either in less than about 10 minutes.

4. The process of claim 3 wherein said support medium is polyacrylamide electrophoresis gel.

5. The process of claim 3 wherein said biopolymers are selected from the group consisting of proteins, nucleic acids and mixtures thereof.

6. The process of claim 3 wherein said support medium is an electrophoresis membrane.

7. The process of claim 6 wherein said membrane is a cellulose nitrate membrane.

8. A process for rapid visualization of separated biopolymers on suitable support medium comprising:
   (a) immersing said support medium for about 5 min in an aqueous solution consisting essentially of about 50% v/v methanol, about 10% v/v acetic acid and about 40% v/v deionized water containing about 2% w/v citric acid and about 0.2% w/v sodium chloride;
   (b) thereafter immediately rinsing said support medium with deionized water to remove surface chloride;
   (c) placing said support medium in a a single photoimaging mixture containing about 50% v/v methanol, about 10% v/v acetic acid and 40% v/v of deionized water containing about 2% w/v silver nitrate, wherein imaging of separated biopolymers appears immediately upon placing said support medium in said photoimaging mixture.

9. The process of claim 8 wherein said support medium is an electrophoresis membrane.

10. The process of claim 9 wherein said membrane is a cellulose nitrate membrane.

* * * * *